(12) United States Patent
Manian

(10) Patent No.: US 6,181,413 B1
(45) Date of Patent: Jan. 30, 2001

(54) DISPLACING VOLUME IN FIELD OF VIEW

(75) Inventor: Bala S. Manian, Los Altos Hills, CA (US)

(73) Assignee: Biometric Imaging, Inc., Mountain View, CA (US)

( * ) Notice: Under 35 U.S.C. 154(b), the term of this patent shall be extended for 0 days.

(21) Appl. No.: 09/390,622

(22) Filed: Sep. 3, 1999

(51) Int. Cl.$^7$ .................................................. G01N 1/28
(52) U.S. Cl. ................................................ 356/36; 356/318
(58) Field of Search ................................... 356/317, 318, 356/417; 250/461.2

(56) References Cited

U.S. PATENT DOCUMENTS

| | | | |
|---|---|---|---|
| 5,355,215 | * 10/1994 | Schroeder et al. | 356/317 |
| 5,547,849 | 8/1996 | Baer et al. | 435/7.24 |

* cited by examiner

Primary Examiner—Richard A. Rosenberger
(74) Attorney, Agent, or Firm—Thomas Schneck; David M. Schneck

(57) ABSTRACT

A method and assay system for the displacement of background from the area surrounding target material allows more sensitive detection. The invention is for use with a system in which specific targets localized at a depth within a container are detected in a liquid containing background material that produces an optical background signal. A displacement liquid is introduced that has a density selected to form a layer encompassing the target material and displacing the material that produces the background signal. The layer of the displacement liquid is sufficient to displace background material from a depth exceeding the depth of field of the detection system. The target material is then optically detected at the depth containing the target material with diminished background allowing greater detection sensitivity.

22 Claims, 2 Drawing Sheets

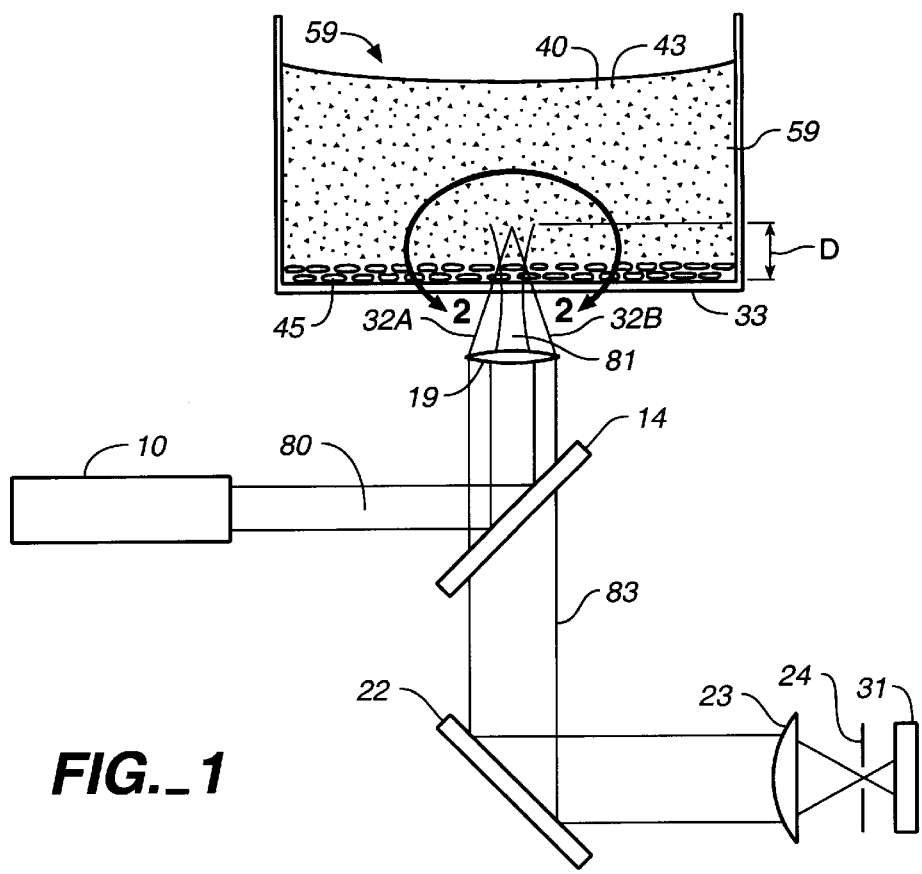
FIG._1
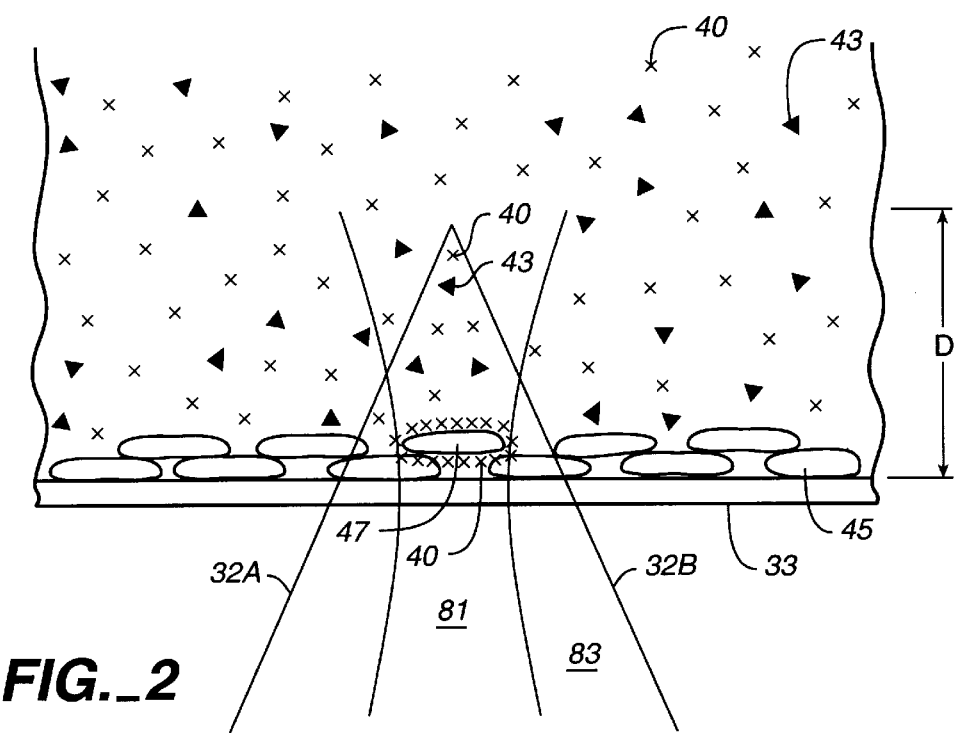
FIG._2

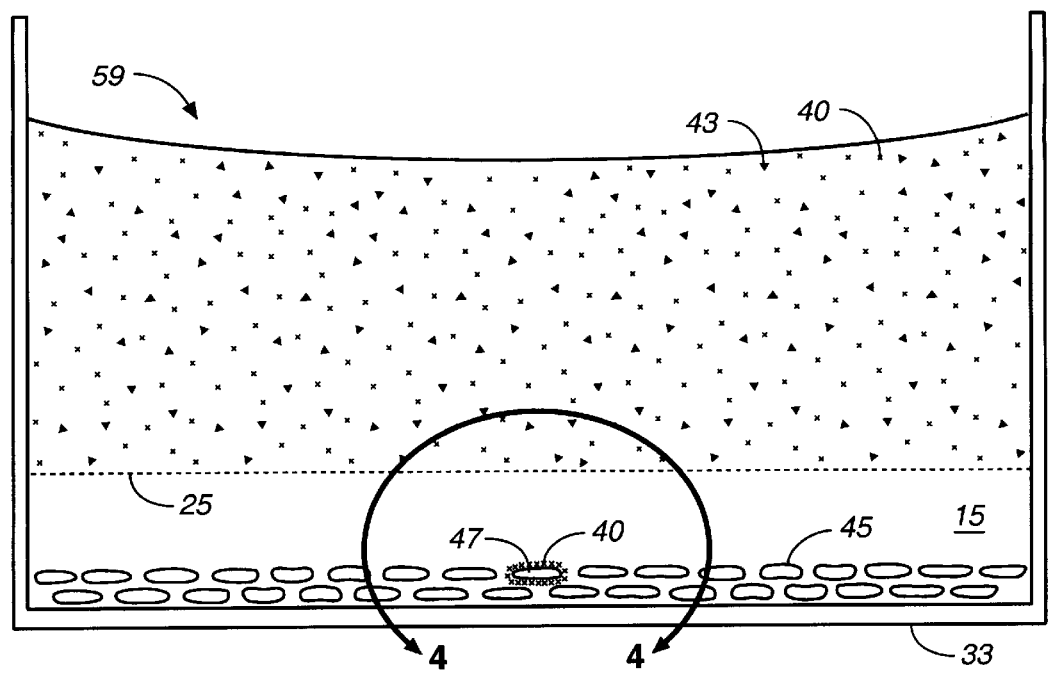
FIG._3
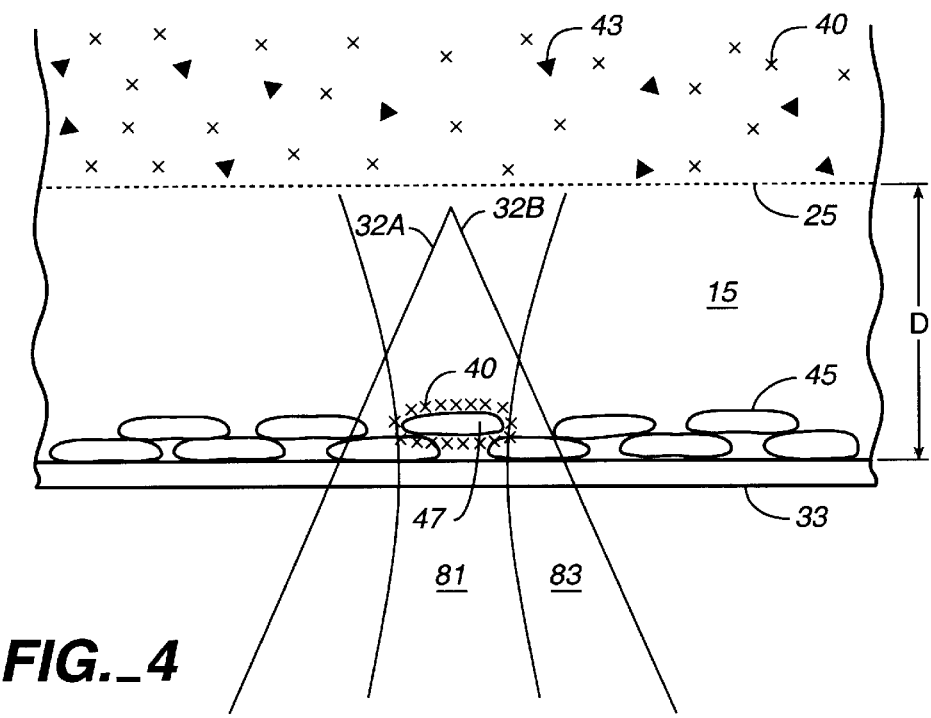
FIG._4

DISPLACING VOLUME IN FIELD OF VIEW

FIELD OF INVENTION

The above invention relates to detection in a limited depth of field and more particularly to minimizing optical background in apparatus methods optically detecting in a limited depth of field.

BACKGROUND ART

The use of optical detection has proved very useful in biological and chemical analytical systems. The use of optically detectable binding agents and optically detectable reactions have provided highly sensitive target detection in analytical systems. The use of a fluorescent label enables highly sensitive detection without the potential hazards of radioactive detection systems. Fluorescent detection may be effected as an array of reactions in separate reaction containers allowing for higher through-put assays. In addition, different markers emitting fluorescence at different wavelengths allow for the simultaneous measurement of multiple parameters in each assay, with each parameter measured with a different optically detectable marker with specific optical properties. Each optical marker would be characterized by a specific detectable emission wavelength. Optical detection may be effected either as in-vitro studies in which compounds bind to a solid support or as in-vivo assays wherein a labeled binding agent selectively binds to an assay target on the cell.

In optical detection assays, the use of detection in a homogenous assay mixture allows rapid detection with minimal processing steps. In such a detection assay, the sample is analyzed without purification steps. The homogenous assay mixture would thus contain the Sample material to be tested and the reagents added to the sample. At least one of the added reagents would react with the sample to form a binding site-binding agent complex to make a target optically detectable. Analyzing the homogenous assay mixture enables detection of the target without purification steps. This decreases assay error, makes the assay more rapid and saves experimentalist time. In addition, absolute target measurement (i.e. target number per unit volume) is enabled by measuring individual targets, such as cells, in a homogenous assay.

One limitation with such optical detection in a homogenous liquid is the optical background. The unbound or unreacted reagent that makes the target optically detectable is present in the reaction mixture. In addition other elements in the reaction mixture, such as components from the unpurified test sample, also cause optical interference. One method to assuage this problem is to use an optical system which directs light of a specific wavelength at the target. This light can be selected to minimize optical interference by providing illumination specifically directed to excite fluorescence from the label on the binding agent but to be outside of the wavelengths which would excite autofluorescence from the sample.

However, this will not solve the problem of optical interference from the unbound or unreacted reagent used as the binding agent to make the target optically detectable. This reagent will have the same optical properties both when bound to the target and when free in the assay mixture. The solution to this problem has been to limit the depth of field for the optical detection system. The targets commonly have a characteristic density or adhere to a solid support at a discrete location. The targets naturally concentrate at one depth with the sample container. If the container contains a density gradient media, the sample will form a band at a specific density layer. Alternatively the assay can be configured so that the targets bind to a static surface at a specific depth within the sample container. In either case the optical detection system need detect only for a limited depth of field. One example of an optical instrument that limits the depth of field is a confocal microscope. Alternatively the IMAGN 2000 from Biometric Imaging combines optical elements to provide a raster line scan of a depth of 25 nm or more within a container. See U.S. Pat. No. 5,547,849. In such a limited depth of field the amount of background measured from the unbound or unreacted reagent would be significantly less than in the total volume. This allows the target, which contains a much higher level of the optically detectable marker associated with the reagent to be detected. However, the amount of the background from the unbound or unreacted reagent is still significant. This lowers the detection threshold for the target compound or complex. In addition, the amount of reagent with associated optically detectable marker added to the assay mixture must be limited to control background. For some assays, adding a higher amount of this reagent may allow improved reaction speed or enable lower levels of detection. However, to reduce background higher levels of binding agent are precluded. A method to separate the assay reagents from the targets band to binding agents is needed.

It is the object of the invention to provide a method of optically detecting targets in a liquid sample containing unbound fluorescent reagents with lower background. This improved method should provide the ability to use a greater range of wavelengths, lower detection limits and possibly increase detection speed.

A further object of the invention is to describe an assay system for the optical detection of targets with reduced background.

SUMMARY OF INVENTION

The above objects are achieved with a method and assay system having a displacement liquid that displaces the homogenous liquid from around the targets in the optical depth of field of an analytical instrument. In the method, a homogenous liquid is introduced into an analytical container. The homogenous liquid is comprised of a sample potentially containing various assay targets and assay reagents. One of the reagents is an optically detectable binding agent that binds to the target which is present both bound to the targets and free in solution. The targets are then allowed to concentrate within the container at a single depth layer within the container. The target concentration is effected by gravitational settling within the container, forming a layer within a density gradient in the container, binding to a solid support located at a specific depth within the container or other methods of target concentration at a specific depth.

A displacement liquid is then added to the container. The displacement liquid has a selected density such that the displacement liquid forms a layer containing the targets within the depth of the container. The displacement liquid is selected such that it does not optically interfere or produce fluorescence at the excitation and emission wavelengths of the optically detectable binding agent. An area within the displacement liquid layer containing the targets of interest is then scanned to detect the targets of interest.

The assay system of the present invention would include a container containing a homogenous assay sample. Also within the container is a displacement liquid for use with the targets of interest. The displacement liquid would be of selected density to displace the volume of liquid from the area surrounding the targets. The system would have an optical detector that optically detects targets in the layer of the displacement liquid.

BRIEF DESCRIPTION OF THE DRAWINGS

FIG. 1 shows a schematic of an optical cytometer detecting targets in an assay mixture contained within a container (shown in cross section).

FIG. 2 shows a detail from FIG. 1 of detection of target cells by the optical cytometer in an assay mixture.

FIG. 3 shows a microplate well containing a background displacement liquid in accord with the present invention.

FIG. 4 shows the detail shown in FIG. 2 with the background displacement liquid included in the container displacing the assay mixture.

DETAILED DESCRIPTION

The invention encompasses the use of a displacement liquid to reduce background in the optical scanning of liquids for detectable targets. As described in the following detailed description, the invention is based on the fact that in assays, the target of interest is often localized at a specific depth within a container. The target either gravitationally settles to this layer or binds to a solid support at this depth. By limiting the depth of field, this layer can be optically scanned without washing or isolating the layer. With the present invention the background from this layer is greatly reduced.

The invention is to be understood with the following definitions:

"Target" is the particle or compound that the assay is directed to detect. The target may be a specific cell type, a class of cells, a cell fragment or component, a protein, a nucleic acid sequence, or other compounds or particles.

"Target cell" refers to a cell type that the assay is directed to detect.

"Homogenous assay mixture" refers to the combination of the sample to be tested and the reaction reagents. To be homogenous requires that no separation step is used to separate target components from the rest of the assay mixture. The reaction reagents include at least one reagent that acts as a binding agent and reacts with a target compound potentially present in the sample and makes this compound optically detectable.

"Optically detectable binding agent" is a compound that binds to the target of interest. Optically detectable binding agents include, but are not limited to, antibodies, single stranded nucleic acids, receptor proteins, and other selectively binding agents. The optically detectable label associated with the binding agent may be an optically detectable dye directly attached to the binding agent. Alternatively the optically detectable label may be a secondary agent that binds to either the target or the binding agent or the target/binding agent in combination.

"Scan depth of field" is the depth within a container that an optical instrument scans. It is from this depth that a system detects emitted fluorescent light. Scan depth of field is limited by optical instrumentation.

"Settling" refers to the concentration of the target to a layer within the container. This concentration may occur as the targets forming an isopycnic band at a depth within the container, the targets gravitationally settling to the bottom of the container, or the targets binding to a solid support at a layer within the container.

"Displacement liquid" refers to a liquid that surrounds the targets and displaces the non-target compounds or particles from a depth within a container.

FIG. 1 shows a schematic of some components of an optical detection system used with a container containing a homogenous assay mixture. The container is shown in cross-section (container not to scale). This system of optical detection is further described in U.S. Pat. Nos. 5,585,246; 5,547,849; 5,556,764; 5,689,110 and Ser. No. 08/698,807 all hereby expressly incorporated by reference herein.

Laser 10 produces laser light 80. Laser light 80 is selected to excite fluorescence from optically labeled binding agent 40. Laser light 80 is directed by dichroic mirror 14 to objective lens 19. Objective lens 19 focuses coherent light 80 into Gaussian waist 81 as the light travels through a transparent container bottom 33 into the interior of container 59.

Coherent light 80 will excite fluorescence from compounds contained within container 59. These compounds will include optically detectable binding agent 40 as well as fluorescent debris 43. The fluorescent light will be emitted by fluorophores in all directions. Some of this fluorescent light will be gathered by the optical system. Lines 32a and 32b define an area of admitted light that will be gathered by the optical system. This light will reach objective lens 19 and be transmitted as a retrobeam to dichroic mirror 14. Dichroic mirror 14 is selected to reflect light of the wavelength of coherent light 80 but allow light of fluorescent light retrobeam 83 to be transmitted through. Fluorescent light retrobeam 83 is then directed by steering mirror 22 to focus lens 23. Focus lens 23 focuses the retrobeam through the aperture of spatial filter 24 onto photodetector 31. Photodetector 31 then produces a measurement of the light intensity of the retrobeam.

The depth of the scan D will be determined by the selection and positioning of the various optical elements. For example, the shape, optical properties and positioning of objective lens 19 will determine the size of the focused Gaussian waist. The positioning and size of aperture 24 will determine the amount of light that passes to photodetector 31. A smaller size of the aperture of spatial filter 24 closer to focus lens 23 results in blocking of additional light from the retrobeam 83 resulting in a shallower depth of field D.

The partial view of FIG. 1 defined by line 2 is shown in FIG. 2. The assay mixture examined contains optically detectable binding agent 40 and fluorescent debris 43. Non-target cells 45 and target cell 47 have gravitationally settled to the transparent container bottom 33. Optically detectable binding agent 40 is selected such that it selectively binds to cell surface antigens on target cell 47.

As shown in FIG. 1, the optical elements of the scanning system limit the depth of the scan to focal depth D. Gaussian waist 81 is directed through transparent container bottom 33 illuminating a column or area of liquid. Fluorophores within this column of liquid that are excited by light of the wavelength of the illuminating light will produce fluorescence. The elements of the optical scanner limit the collection of fluorescent light to the area represented by lines 32a and 32b.

Contained between lines 32a and 32b and illuminated by the light of Gaussian waist 81 is target cell 47 with optically detectable binding agent 40 bound to its surface. Also within this area are an amount of optically detectable binding agent 40 free in solution and some fluorescent debris 43. The fluorescence generated by optically detectable binding agent 40 and fluorescent debris 43 will be transmitted at retrobeam 83 to a photodetector as shown in FIG. 1. Because detection is effected in a limited depth of field the detector may detect the target cell in the presence of optical background of unbound binding agent.

FIG. 3 shows the container containing the assay mixture and also containing displacement liquid 15. Displacement liquid 15 has sufficient density such that it has sunk to the bottom of container 59 resting upon transparent container bottom 33. Liquid containing unbound optically detectable binding agent 40 and fluorescent debris 43 has been displaced to above the location of displacement liquid 15. Non-target cells 45 and target cell 47 are positioned on the bottom of the container resting on transparent container bottom 33.

The area defined by line 4 of FIG. 3 is shown in FIG. 4. In this figure, displacement liquid 15 has displaced the liquid containing unbound optically detectable binding agent 40 and fluorescent debris 43. As in FIG. 2 the Gaussian waist 81 extends through transparent container bottom 33 to illuminate a column or area of liquid within the well. Lines 32 and 32b define an area from which the optical system will detect fluorescent light. This light will be transmitted as retrobeam 83 and directed by the optical elements shown in FIG. 1 to a photodetector. Within the depth of field D displacement liquid 15 has displaced all elements except for non-target cells 45 and target cell 47. Bound to target cell 47 is optically detectable binding agent 40. Because displacement liquid 15 has displaced other potential sources of fluorescent signal the remaining source of fluorescent signal will be the optically detectable binding agent 40 bound to target cell 47. This greatly reduces the background allowing for a lower detection threshold.

The disclosed displacement liquid may be used in a number of different assays. These assays include detection of protein with labeled antibodies and detection of cells with labeled antibodies. When antibodies are used it is preferred to use monoclonal antibodies which have high specificity. Other assays include detection of nucleic acids with labeled probes (either in situ or bound to beads) and assays using fluorescent reporter beads. The targets may be free in solution or bound to a solid support. For example, the bottom of the container may be used as a solid support to which targets bind. The container may have binding properties such that the target binds to the surface. The targets may then be optically labeled and detected. In addition, it is possible to use optically detectable beads as a solid support. Reporter beads produce a fluorescence in response to certain assay conditions. Such beads may be used to monitor pH or other assay conditions. It is also possible to use beads that have receptors bound to the beads surfaces. The receptors bind to a labeled target, such as a protein or cell. The bead with bound targets is then detected.

In these assays, the optically detectable target may be optically detectable in a number of ways. The target may be directly detected with a fluorescently labeled binding agent or a secondary reporter may indicate the presence of the target. A number of different optically detectable moieties may be used with the present invention. These include short-lived chemiluminescent markers, fluorescent microbeads that are associated with the target of interest, fluorescently dyes conjugated to a binding agent or other optically detectable markers. If a fluorescent marker is used, it is preferred to have label on the binding agent be a fluorescent dye that has an excitation and emission wavelength between 400 and 1000 nm. In whole blood assay dyes with excitation and emission wavelengths above 600 nm are preferred. This range of wavelengths is outside of the range in which most biological sample material will produce autofluorescence. This helps to minimize background.

These assays may be carried out in a number of different containers. These include capillaries (such as rectangular capillaries), cuvettes, and microplate wells. Microplates allow the advantage of parallel sample processing and higher throughput potential.

The displacement agent is added to a well to displace the solution in the well that contains the unbound fluorescent binding agent, fluorescent debris, and other non-target compounds. This compound would be added after the cells or particles have settled to a layer within a container. The compound would be required to have three properties:

1. The compound should have a selected density such that the targets are isolated within the compound while other non-target reagents or debris are displaced. If beads or cells are the target, these targets would generally gravitationally settle to the bottom of the container. The displacement liquid would be sufficiently dense to also sink to the bottom of the well and form a layer about the cells.
2. The compound would not go into solution with the reagents used in the assay. The viscosity or chemical properties of the solution would favor displacement of the reagents over combination with the reagents.
3. The compound should not produce fluorescence or optically interfere with the detection of the optical label associated with the target.

Suitable compounds that meet this criteria include organosilinized colloidal silica, silica sol coated with non-dialysable polyvinylpyrrolidone, dextran, a solution of hydrophilic polymers of sucrose, and other compound. These compounds may be mixed with various buffers to produce a desired concentration. These compounds may be used alone or in combination with various buffers, media, polylactams, or other compounds to realize a desired osmolarity, pH, density, or other desired displacement liquid property. These are dependent on associated assay.

Because the depth of field is fairly small (as low as 25 nm), only a small amount of this displacement compound needs to be added to a well to displace the liquid in the depth of field. Preferably the displacement liquid layer is at least two time the detection depth of field to assure minimal optical interference from non-target moieties. The step of adding this liquid adds nearly no error to the procedure, does not require removal of liquids or washing cells, requires minimal additional time and has a low reagent cost. It enhances the sensitivity of assays and allows the assays to tolerate higher levels of the optically detectable compounds, such as an optically labeled binding agent.

Various alternatives are possible with the use of the liquid. It is possible to apply a centrifugal force to the container to make the displacement more rapid. If this is done, the displacement liquid and centrifuge speed would be selected to minimize cell shearing.

It may be desirable to locate the interface between the displacement liquid and the displaced liquid. This would allow the measurement of the amount of unreacted binding agent by fluorescent detection. To do this the interface may be located. U.S. Pat. No. 5,556,764 describes one method of interface localization. In this method the surface is moved relative to the waist of the focused laser. When the waist is below the interface minimal fluorescent emission will be measured. When the waist is fully above the interface a maximum fluorescent emission will be measured. A second method to locate this interface layer is taught in U.S. Ser. No. 09/245,782 hereby expressly incorporated by reference herein. This method again requires movement of the well in relation to the focused Gaussian waist. Specular reflection from the interface is collected. When specular reflection is at a maximum the waist of the beam is focused onto the interface.

I claim:

1. A method to optically detect target substances in a liquid, the method comprised of the steps of:

adding a liquid sample to a sample container, the sample comprised of optically detectable targets of a specific density range as well as other non-target compounds, said targets and compounds producing an optical signal;

allowing the targets to settle within said sample container such that a majority of the detectable targets are contained within a specific depth within the container;

adding a displacement liquid to the container, the displacement liquid selected to settle at the specific depth of the layer containing the detectable targets; and optically scanning said container, said step of optically scanning effected in a scan depth of field limited to within the depth of the displacement liquid within the sample container.

2. The method of claim 1 in which the step of optically scanning the container is effected wherein the scan depth of field that is half as deep as the depth of the displacement liquid.

3. The method of claim 1 wherein the step of allowing the targets to settle within the sample container is effected by allowing the targets to gravitationally settle to the depth within the container.

4. The method of claim 1 wherein the step of allowing the targets to settle within the sample container is effected by allowing the targets to bind to a solid support present at the depth within the container.

5. The method of claim 1 wherein the step of allowing the targets to settle within the sample container is effected by binding the targets to beads and allowing the beads to gravitationally settle to the depth within the container.

6. The method of claim 1 further comprising the step of optically detecting the location of an interface layer between said displacement liquid and a liquid displaced by said displacement liquid.

7. The method of claim 6 wherein the step of detecting the interface layer is effected by localizing specular reflection from the interface layer.

8. The method of claim 6 wherein the step of detecting the interface layer is effected by localizing fluorescence.

9. The method of claim 6 further comprising measuring the optical signal from the non-target compounds in the liquid displaced by said displacement liquid.

10. A method of optically detecting target cells in a plurality of microplate wells, the method comprised of the steps of:

adding a liquid sample to the plurality of wells within the microplate, the liquid sample comprised of a cell sample potentially containing target cells and an optically detectable selective binding agent, said binding agent selectively binding to target cells wherein said optically detectable binding agent is present both unbound in solution and potentially bound to target cells present;

allowing the target cells to gravitationally settle to a bottom of said plurality of wells;

adding a displacement liquid into said plurality of wells, such that a layer is formed containing the displacement liquid and the gravitationally settled target cells but substantially displacing the unbound binding agent;

optically scanning with a limited scan depth of field within the layer of displacement liquid to optically detect the target cells.

11. An assay system for the detection of targets in reduced background, the system comprising:

a container;

an assay mixture contained in said container, the assay mixture comprised of a test sample having an optically detectable binding agent capable of selective binding to targets present in said test sample, wherein said present targets settle to a depth with the container;

a displacement liquid contained in said container, said displacement liquid having a density selected such that the displacement liquid forms a layer within said container, said layer containing said target and displacing unbound optically detectable binding agent from said layer;

an optical system directing focused laser light into said container, said light exciting fluorescence from said targets present, said fluorescence detected from a limited depth of field within the container, said depth of field limited to within said layer of said displacement liquid.

12. The assay system of claim 11 wherein the container is a rectangular capillary.

13. The assay system of claim 11 wherein the container is a well on a microplate.

14. The assay system of claim 11 wherein the target is a type of cell.

15. The assay system of claim 14 wherein the optically detectable binding agent is a fluorescently labeled antibody.

16. The assay system of claim 14 wherein the optically detectable binding agent is a fluorescently labeled nucleic acid probe.

17. The assay system of claim 11 wherein the target is a nucleic acid.

18. The assay system of claim 17 wherein the optically detectable binding agent is a fluorescently labeled single strand of DNA.

19. The assay system of claim 11 wherein the target is a protein.

20. The assay system of claim 19 wherein the optically detectable binding agent is a fluorescently labeled monoclonal antibody that selectively binds to said protein.

21. The assay system of claim 11 wherein the target is a fluorescent bead.

22. The assay system of claim 11 wherein the displacement liquid is selected from the group comprised of hydrophylic polymers of sucrose, polyvinylpropoline coated silica particles, dextran, and organosilinized colloidal silica.

* * * * *